US009403770B2

(12) United States Patent
Bertolini et al.

(10) Patent No.: US 9,403,770 B2
(45) Date of Patent: Aug. 2, 2016

(54) PROCESS FOR PREPARING FEXOFENADINE

(75) Inventors: Giorgio Bertolini, Milan (IT); Maurizio Gallina, Novara (IT); Giuseppe Motta, Milan (IT); Domenico Vergani, Biassono (IT)

(73) Assignee: Euticals SPA, Milan (IT)

( * ) Notice: Subject to any disclaimer, the term of this patent is extended or adjusted under 35 U.S.C. 154(b) by 1017 days.

(21) Appl. No.: 12/374,539

(22) PCT Filed: Jul. 25, 2007

(86) PCT No.: PCT/IT2007/000525
§ 371 (c)(1),
(2), (4) Date: Jan. 21, 2009

(87) PCT Pub. No.: WO2008/012858
PCT Pub. Date: Jan. 31, 2008

(65) Prior Publication Data
US 2011/0190504 A1 Aug. 4, 2011

(30) Foreign Application Priority Data
Jul. 27, 2006 (IT) .............................. MI2006A1492

(51) Int. Cl.
C07D 211/22 (2006.01)
(52) U.S. Cl.
CPC .................................... C07D 211/22 (2013.01)
(58) Field of Classification Search
CPC ........................... C07D 211/43; A61K 311/445
USPC ....................................................... 546/239
See application file for complete search history.

(56) References Cited

U.S. PATENT DOCUMENTS

| 4,254,129 A | | 3/1981 | Carr et al. | |
|---|---|---|---|---|
| 5,136,070 A | * | 8/1992 | Bank | 556/469 |
| 5,663,412 A | * | 9/1997 | D'Ambra | 560/51 |
| 2002/0111513 A1 | | 8/2002 | Ayers | |
| 2003/0105329 A1 | | 6/2003 | Schroeder et al. | |
| 2003/0171590 A1 | | 9/2003 | D'Ambra et al. | |
| 2003/0220496 A1 | | 11/2003 | Krauss et al. | |
| 2005/0282860 A1 | * | 12/2005 | Castaldi et al. | 514/317 |
| 2006/0148851 A1 | * | 7/2006 | Wizel et al. | 514/317 |

FOREIGN PATENT DOCUMENTS

| EP | 1 614 681 A1 | 1/2006 |
|---|---|---|
| WO | WO 2006/037042 A1 | 4/2006 |

OTHER PUBLICATIONS

Aldrich catalog, p. 1-2 (2012).*
Ivashchenko et al. "Preparation, . . . " WJNSE v.2, p. 117-125 (2012).*
Yabe et al. "New aspect of . . . " Cat. Sci. Tech. (2013) p. 1-10, accepted manuscript (2013).*
Wizel "Preparation of a polymorphic . . . " CA144:350552 (2006).*
Carbonyl reduction, Wikepedia p. 1-2 (2015).*
Tiedtke et al. "Chemicals influencing . . . " 13$^{th}$ Ethylene producers' conference, v.10 p. 1-21 (2001).*

* cited by examiner

Primary Examiner — Celia Chang
(74) Attorney, Agent, or Firm — ProPat, L.L.C.

(57) ABSTRACT

A process for preparing fexofenadine is described, which provides for the hydrolysis of 4-[4-[4-(hydroxydiphenylmethyl)-1-piperidyl]-1-oxobutyl]-α,α-dimethylbenzeneacetic acid-alkyl ester, in a mixture of water and optionally an organic solvent, in the presence of a base; the carboxylate salt of 4-[4-[4-(hydroxydiphenylmethyl)-1-piperidyl]-1-oxobutyl]-α,α-dimethylbenzeneacetic acid is thus obtained, which is then directly reduced as carboxylate in a basic environment with hydrogen in the presence of a suitable hydrogenation catalyst to give the carboxylate of fexofenadine, which is precipitated by neutralization of the solution.

16 Claims, No Drawings

PROCESS FOR PREPARING FEXOFENADINE

CROSS-REFERENCE TO RELATED APPLICATIONS

This application is being filed under Rule 1.371 as a National Stage Application of pending International Application No. PCT/IT2007/000525 filed Jul. 25, 2007, which claims priority to the following parent application: Italian Patent Application No. MI2006A001492, filed Jul. 27, 2006. Both International Application No. PCT/IT2007/000525 and Italian Patent Application No. MI2006A001492 are hereby incorporated by reference herein in their entirety.

FIELD OF THE INVENTION

Process for preparing fexofenadine comprising the hydrolysis of 4-[4-[4-(hydroxydiphenylmethyl)-1-piperidyl]-1-oxobutyl]-α,α-dimethylbenzeneacetic acid-alkyl ester to 4-[4-[4-(hydroxydiphenylmethyl)-1-piperidyl]-1-oxobutyl]-α,α-dimethylbenzeneacetic acid which is catalytically hydrogenated as fexofenadine carboxylate salt.

BACKGROUND OF THE INVENTION

Summary of Advantageous Embodiments of the Invention

The present invention concerns a process for preparing fexofenadine, the formula (I) of which is shown below:

FORMULA I

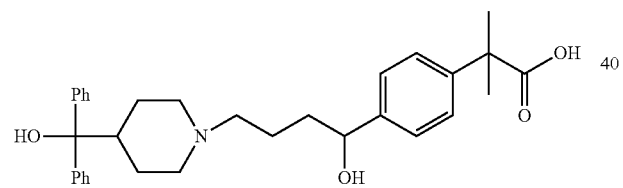

The process provides for the hydrolysis of 4-[4-[4-(hydroxydiphenylmethyl)-1-piperidyl]-1-oxobutyl]-α,α-dimethylbenzeneacetic acid-alkyl ester, shown below as formula (II),

FORMULA II

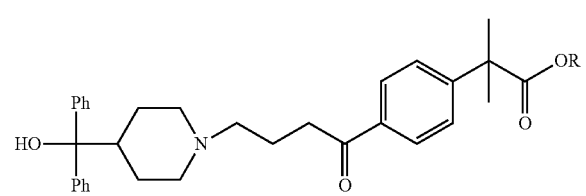

where R is an alkyl group, in a mixture of water and optionally an organic solvent, in the presence of a base by obtaining the carboxylate salt of 4-[4-[4-(hydroxidiphenylmethyl)-1-piperidyl]-1-oxobutyl]-α,α-dimethylbenzeneacetic acid, shown below as formula (III),

FORMULA III

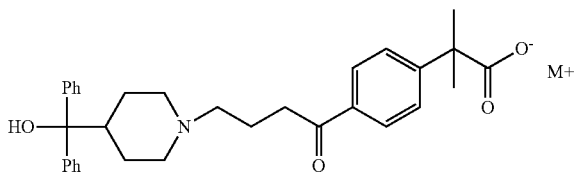

where M+ is the cation of the carboxylate salt (or, in other words, the cation of the base used for the hydrolysis), which is directly reduced as carboxylate in a basic environment with hydrogen in the presence of a suitable catalyst to give the carboxylate of fexofenadine, which is precipitated by neutralisation of the solution.

The processes of preparing fexofenadine starting from the compound of formula II reported in the literature describe as a preferred method of ketone group reduction the reduction with sodium borohydride as, for example, described in U.S. Pat. No. 4,254,129. This reaction may be carried out before or after the ester hydrolysis. The methods of catalytic reduction mentioned are described as less efficient. These reactions are conducted in organic solvents on the compound of Formula II or its relative acid. Under these conditions, the reaction yields have proven to be quite low because of the formation of an impurity caused by the complete hydrogenolysis and the loss of one or both oxygens at benzyl position and which makes up about 32% of the product deriving from the hydrogenolysis.

DESCRIPTION OF THE INVENTION

In the new process, the compound of FORMULA II

FORMULA II

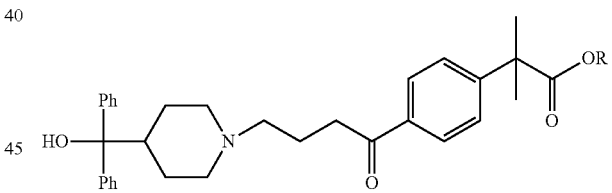

where R is an alkyl group, preferably a $C_1$-$C_4$ alkyl group, still more preferably methyl, is dissolved or suspended in a mixture of organic solvent and water, in the presence of a base, or in water and base only, and hydrolysed under stirring at a temperature comprised between 0° C. and the reflux temperature of the mixture. The organic solvent is preferably a polar solvent, normally of a protic type, preferably a $C_1$-$C_4$ alcohol, still more preferably methanol. The base is preferably of an inorganic nature, such as, for example, the hydroxide of an alkaline or alkaline-earth metal, still more preferably NaOH.

Said organic solvent, when used, is present in ratios in the range of 0.25-16 volumes in relation to water; or said mixture of water and organic solvent is preferably present in 6-7 volumes in relation to compound II; the base, in turn, is preferably used in molar excess in relation to the compound of formula II, preferably with a molar ratio from 3 to 5.

The compound of FORMULA III is obtained from this reaction

FORMULA III

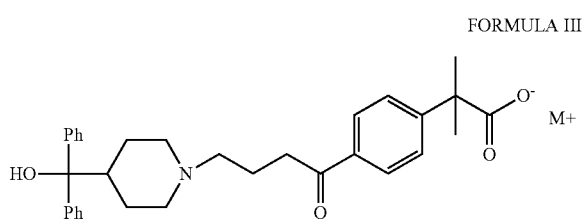

where M+ is the cation of the carboxylate salt, preferably Na+.

A suitable metallic-type hydrogenation catalyst is added to the system thus obtained, preferably selected from suitably supported palladium, platinum, or ruthenium (preferably palladium on carbon) and is hydrogenated at a temperature between 0° C. and the boiling point of the solvent at a pressure in the range of 1-100 bar, preferably 1-10 bar.

Fexofenadine, FORMULA I, is obtained from the hydrogenation reaction

FORMULA I

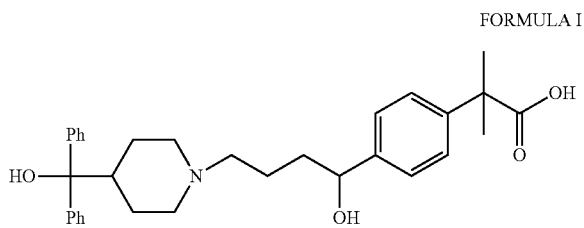 [SMILES: CC(C)(C(=O)O)c1ccc(C(O)CCCN2CCC(C(O)(c3ccccc3)c3ccccc3)CC2)cc1]

which is then precipitated by neutralising the base present in solution with an acid, preferably acetic acid.

The examples which follow are purely illustrative and non limiting of the invention.

EXAMPLE 1

In a four-necked flask equipped with a mechanical stirrer, 100 g of 4-[4-[4-(hydroxydiphenylmethyl)-1-piperidyl]-1-oxobutyl]-α,α-dimethylbenzeneacetic acid-methyl ester, 600 ml of methanol and 60 ml of 30% sodium hydroxide are loaded. The mixture is heated at reflux and kept under stirring for about 5 hours. When the ester is completely hydrolysed, 10 g of 5% palladium on carbon are loaded into the reactor and are hydrogenated at 50° C. and 6 bar pressure until the complete conversion of the benzylketone into the corresponding alcohol. Once the reaction is completed, the catalyst is filtered and the fexofenadine is precipitated by adjusting the pH to 5-8 with acetic acid. The solid obtained is filtered and dried under vacuum at 65° C.

85 g of crude fexofenadine are obtained on average with HPLC purity >99%. Optimum temperature for hydrogenation: 35-45° C.; pH of precipitation 5-6.

EXAMPLE 2

In a four-necked flask equipped with a mechanical stirrer, 100 g of 4-[4-[4-(hydroxydiphenylmethyl)-1-piperidyl]-1-oxobutyl]-α,α-dimethylbenzeneacetic acid-methyl ester, 600 ml of water, 150 ml of Isopropanol and 73 ml of 30% sodium hydroxide are loaded. The mixture is heated at reflux and kept under stirring for about 5 hours. When the ester is completely hydrolysed, 10 g of 5% palladium on carbon are loaded into the reactor and are hydrogenated at 50° C. and 6 bar pressure until the complete conversion of the benzylke-tone into the corresponding alcohol. Once the reaction is completed, the catalyst is filtered and the fexofenadine is precipitated by adjusting the pH to 5-8 with acetic acid. The solid obtained is filtered and dried under vacuum at 65° C.

85 g of crude fexofenadine are obtained on average with HPLC purity >99%. Optimum temperature for hydrogenation: 35-45° C.; pH of precipitation 5-6.

EXAMPLE 3

In a four-necked flask equipped with a mechanical stirrer, 100 g of 4-[4-[4-(hydroxydiphenylmethyl)-1-piperidyl]-1-oxobutyl]-α,α-dimethylbenzeneacetic acid-methyl ester, 600 ml of methanol and 60 ml of 30% sodium hydroxide are loaded. The mixture is heated at reflux and kept under stirring for about 5 hours. When the ester is completely hydrolysed, 10 g of 5% palladium on carbon are loaded into the reactor and are hydrogenated at 50° C. and 10 bar pressure until the complete conversion of the benzylketone into the corresponding alcohol. Once the reaction is completed, the catalyst is filtered and the fexofenadine is precipitated by adjusting the pH to 5-8 with acetic acid. The solid obtained is filtered and dried under vacuum at 65° C.

85 g of crude fexofenadine are obtained on average with HPLC purity >99%. Optimum temperature for hydrogenation: 35-45° C.; pH of precipitation 5-6.

EXAMPLE 4

In a four-necked flask equipped with a mechanical stirrer, 100 g of 4-[4-[4-(hydroxydiphenylmethyl)-1-piperidyl]-1-oxobutyl]-α,α-dimethylbenzeneacetic acid-methyl ester and 600 ml of methanol are loaded. When the ester is completely solubilised, 10 g of 5% palladium on carbon are loaded into the reactor and are hydrogenated at 50° C. and 6 bar pressure until the complete conversion of the benzylketone into the corresponding alcohol. Once the reaction is completed, the catalyst is filtered, 60 ml of 30% sodium hydroxide are added and the mixture is heated at reflux and kept under stirring until the complete hydrolysis of the ester, about 5 hours. The fexofenadine is precipitated by adjusting the pH to 5-8 with acetic acid. The solid obtained is filtered and dried under vacuum at 65° C.

55 g of fexofenadine are obtained with HPLC purity of about 60% and an impurity with A % equal to 32, which, from the calculation of the molecular weight, has one less oxygen.

The invention claimed is:

1. A process for preparing fexofenadine comprising hydrolysing a compound of formula

II

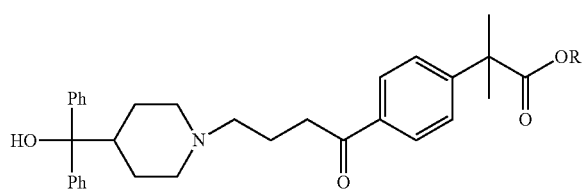

where R is an alkyl group, in the presence of a base to give the compound of formula

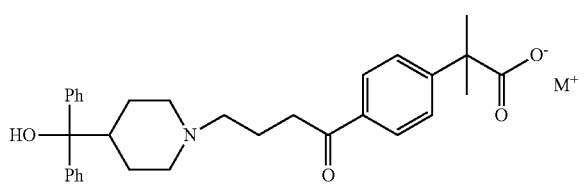

where M+ is the cation of the carboxylate salt, and subsequently hydrogenating the compound of formula III in the presence of a hydrogenation catalyst to give fexofenadine, wherein said compound of formula II is dissolved or suspended in a $C_1$-$C_4$ alcohol; water or a mixture of water and $C_1$-$C_4$ alcohol, said catalyst is palladium supported on carbon, and said hydrogenation is performed in a basic environment with hydrogen.

2. A process according to claim 1, wherein R is a $C_1$-$C_4$ alkyl group.

3. A process according to claim 1, wherein said organic solvent is present in ratios in the range of 0.25-16 volumes in relation to water.

4. A process according to claim 1, wherein said mixture of water and organic solvent is present in 6-7 volumes in relation to the compound.

5. A process according to claim 1, wherein said base is used in molar excess in relation to the compound of formula II.

6. A process according to claim 1, wherein said base is the hydroxide of an alkaline or alkaline-earth metal.

7. A process according to claim 1, wherein M+ is Na+.

8. A process according to claim 1, wherein said hydrogenation is carried out at a temperature between 0° C. and the boiling point of the solvent.

9. A process according to claim 1, wherein said hydrogenation is carried out at it pressure in the range of 1-100 bar.

10. A process according to claim 2, wherein R is methyl.

11. A process according to claim 1, wherein said organic solvent is methanol.

12. A process according to claim 5, wherein said base is used in molar ratio of from 3 to 5 in relation to the compound of formula II.

13. A process according to claim 6, wherein said base is NaOH.

14. A process according to claim 9, wherein said hydrogenation is carried out at a pressure in the range of 1-10 bar.

15. A process according to claim 1, wherein said catalyst is 5% palladium on carbon.

16. A process according to claim 1, wherein said fexofenadine has an HPLC purity higher than 99% directly after precipitation, filtration and drying.

* * * * *